US011109905B2

(12) United States Patent
Vogt et al.

(10) Patent No.: US 11,109,905 B2
(45) Date of Patent: Sep. 7, 2021

(54) BONE CEMENT APPLICATOR WITH RETRACTABLE MIXING ROD AND METHOD FOR PRODUCTION OF A BONE CEMENT

(71) Applicant: Heraeus Medical GmbH, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 255 days.

(21) Appl. No.: 16/443,158

(22) Filed: Jun. 17, 2019

(65) Prior Publication Data

US 2019/0380758 A1 Dec. 19, 2019

(30) Foreign Application Priority Data

Jun. 18, 2018 (DE) .......................... 102018209807.7

(51) Int. Cl.
*A61B 17/88* (2006.01)
(52) U.S. Cl.
CPC .. *A61B 17/8822* (2013.01); *A61B 2017/8838* (2013.01)
(58) Field of Classification Search
CPC ............ A61B 17/8802; A61B 17/8805; A61B 17/8811; A61B 17/8816; A61B 17/8822;
(Continued)

(56) References Cited

U.S. PATENT DOCUMENTS

| 4,671,263 | A | 6/1987 | Draenert |
| 4,758,096 | A | 7/1988 | Gunnarsson |

(Continued)

FOREIGN PATENT DOCUMENTS

| DE | 3640279 | 6/1987 |
| DE | 102016121607 | 6/1987 |

(Continued)

OTHER PUBLICATIONS

Charnley, "Anchorage of the femoral head prosthesis of the shaft of the femur", The Journal of Bone and Joint Surgery, 1960, 42, pp. 28-30. —.

(Continued)

*Primary Examiner* — Matthew J Lawson
(74) *Attorney, Agent, or Firm* — Stradley Ronon Stevens & Young, LLP

(57) ABSTRACT

A bone cement applicator comprising a cartridge with an internal space. The cartridge has a head with a dispensing opening for expulsion of bone cement, a first thread, a dispensing plunger, a threaded tube having a counter thread engaging the first thread, a receptacle mobile in the threaded tube, and a mixing rod with a mixer fastened to it and arranged in the internal space of the cartridge. The mixing rod is detachably connected to the receptacle and is guided through a feedthrough in the dispensing plunger and is supported in the feedthrough so as to be axially mobile. When detached from the receptacle, the mixing rod can be pushed into the receptacle when the receptacle is propelled in the direction of the cartridge head. A method is also disclosed for production of a bone cement using the bone cement applicator.

15 Claims, 8 Drawing Sheets

(58) Field of Classification Search
CPC ............ A61B 17/8825; A61B 17/8827; A61B 17/8838
See application file for complete search history.

(56) References Cited

U.S. PATENT DOCUMENTS

| | | | |
|---|---|---|---|
| 4,973,168 A | 11/1990 | Chan | |
| 5,100,241 A | 3/1992 | Chan | |
| 5,344,232 A | 9/1994 | Nelson et al. | |
| 5,551,778 A | 9/1996 | Hauke et al. | |
| 5,586,821 A | 12/1996 | Bonitati et al. | |
| 5,588,745 A | 12/1996 | Tanaka et al. | |
| 5,624,184 A | 4/1997 | Chan | |
| 5,997,544 A | 12/1999 | Nies et al. | |
| 6,033,105 A | 3/2000 | Barker et al. | |
| 6,709,149 B1 | 3/2004 | Tepic | |
| 7,073,936 B1* | 7/2006 | Jonsson | B01F 15/0279 366/139 |
| 8,757,866 B2 | 6/2014 | Vogt et al. | |
| 2003/0012079 A1* | 1/2003 | Coffeen | B01F 11/0082 366/130 |
| 2009/0149860 A1* | 6/2009 | Scribner | A61B 17/8822 606/93 |
| 2018/0132919 A1* | 5/2018 | Vogt | B01F 15/00954 |

FOREIGN PATENT DOCUMENTS

| | | |
|---|---|---|
| DE | 102009031178 | 9/2010 |
| EP | 0692229 | 1/1996 |
| EP | 0796653 | 9/1997 |
| EP | 1005901 | 6/2000 |
| EP | 1020167 | 7/2000 |
| EP | 1886647 | 2/2008 |
| EP | 1016452 | 6/2019 |
| WO | 9426403 | 11/1994 |
| WO | 9718031 | 5/1997 |
| WO | 9967015 | 12/1999 |
| WO | 0035506 | 6/2000 |

OTHER PUBLICATIONS

Office Action (and English translation) dated Jan. 18, 2019 from counterpart German Patent Application No. 102018209784.4.

* cited by examiner

US 11,109,905 B2

BONE CEMENT APPLICATOR WITH RETRACTABLE MIXING ROD AND METHOD FOR PRODUCTION OF A BONE CEMENT

RELATED APPLICATION

This application claims the benefit of priority to German Patent Application Number DE 10 2018 209 807.7, filed on Jun. 18, 2018, the contents of which are incorporated in this application by reference.

TECHNICAL FIELD

The invention relates to a bone cement applicator for storage and mixing of a bone cement powder and a monomer liquid as well as for applying a pasty bone cement mixed together from the bone cement powder and the monomer liquid. The invention also relates to a method for production of a bone cement using said bone cement applicator.

BACKGROUND OF THE DISCLOSURE

Polymethylmethacrylate (PMMA) bone cements are based on the pioneering work of Sir Charnley. Charnley, J., "Anchorage of the femoral head prosthesis of the shaft of the femur," J. Bone Joint Surg. 42, 28-30 (1960). Conventional PMMA bone cements consist of a liquid monomer component and a powder component. The monomer component generally contains the monomer, methylmethacrylate, and an activator (N,N-dimethyl-p-toluidine) dissolved therein. The powder component, also called bone cement powder, comprises one or more polymers that are produced through polymerization, preferably suspension polymerization, based on methylmethacrylate and co-monomers, such as styrene, methylacrylate or similar monomers, a radiopaquer, and the initiator, dibenzoylperoxide. Mixing the powder component and the monomer component and swelling of the polymers of the powder component in the methylmethacrylate generates dough that can be shaped plastically and is the actual bone cement or bone cement dough. During the mixing of the powder component and the monomer component, the activator, N,N-dimethyl-p-toluidine, reacts with dibenzoylperoxide while forming radicals. The radicals thus formed trigger the radical polymerization of the methylmethacrylate. Upon advancing polymerization of the methylmethacrylate, the viscosity of the bone cement dough increases until the bone cement dough solidifies.

PMMA bone cements can be mixed by mixing the bone cement powder and the monomer liquid in suitable mixing beakers with the aid of spatulas. This can lead to air bubbles being enclosed in the bone cement dough, which can have a negative effect on the mechanical properties of the cured bone cement.

A large number of vacuum cementing systems have been described for preventing air inclusions in bone cement dough of which the following are identified for exemplary purposes: U.S. Pat. Nos. 6,033,105 A, 5,624,184 A, 4,671, 263 A, 4,973,168 A, 5,100,241 A, WO 99/67015 A1, EP 1 020 167 A2, U.S. Pat. No. 5,586,821 A, EP 1 016 452 A2, DE 36 40 279 A1, WO 94/26403 A1, EP 1 005 901 A2, EP 1 886 647 A1, and U.S. Pat. No. 5,344,232 A. These mixing systems contain, for mixing of the cement components, a mixing rod that can be operated manually from outside and has mixing vanes as mixers attached to it. External vacuum pumps are required for generation of the vacuum. These vacuum pumps are generally driven by compressed air and generate a vacuum according to the Venturi principle. Manually driven extrusion devices are used for extrusion of the mixed bone cement from the cartridges. These extrusion devices can be connected reversibly to the cartridges for extrusion of the cement dough. Following the extrusion process, the extrusion devices are separated from the cartridges, cleaned, and re-sterilized. The spent cartridges are discarded.

Cementing systems in which both the bone cement powder and the monomer liquid are already packed in separate compartments of the mixing devices and are mixed with each other in the cementing system only right before application of the cement are a development of cementing technology. Such closed full-prepacked mixing devices have been proposed in EP 0 692 229 A1, DE 10 2009 031 178 B3, U.S. Pat. Nos. 5,997,544 A, 6,709,149 B1, WO 00/35506 A1, EP 0 796 653 A2, and U.S. Pat. No. 5,588,745 A.

Patent DE 10 2009 031 178 B3 discloses a storage and mixing device as a full-prepacked mixing device, in which the starting components required for the production of the bone cement are already stored in the storage and mixing device and can be combined and mixed in the storage and mixing device. The storage and mixing device comprises a two-part dispensing plunger for closing a cement cartridge. A combination of a gas-permeable sterilization plunger and a gas-impermeable sealing plunger is used in this context. This principle of a closed vacuum mixing system is implemented in the closed cementing system made and distributed under the brand name PALACOS® PRO by Heraeus Medical GmbH. For the monomer transfer and the mixing in a vacuum, an external vacuum pump is required that is usually driven by compressed air. Likewise, a separate manually operable extrusion device is used for extruding the mixed cement dough.

DE 10 2016 121 607 A1 proposes a full-prepacked mixing system with a cartridge containing a bone cement powder for production of a bone cement. A dispensing plunger is provided in the cartridge and a receptacle housing a monomer liquid container is arranged downstream from the cartridge. A dispensing plunger is situated on the rear side of the receptacle and can be used to crush the monomer liquid container and to extrude the monomer liquid from the receptacle into the cartridge. This system involves no manual mixing of the starting components by a mixer.

In the vacuum mixing systems with mixers referred to thus far, the mixing of the cement components must be followed by the mixing rod having to be broken off or pulled out of the mixing system before application of the bone cement. Accordingly, the known methods and devices are disadvantageous in that the process of breaking off the mixing rod may be associated with leakage of the bone cement applicator and in that the processes of breaking off and pulling out the mixing rod are always required as additional working steps. Moreover, the broken off mixing rod litters the operating room or "OR" theatre as another separate part that needs to be discarded. Bone cement applicators without a mixer require much effort for the bone cement to be mixed sufficiently. Moreover, it is also possible that parts of the bone cement are not mixed sufficiently. These parts need to be removed or there may be an adverse effect on the quality of the bone cement.

SUMMARY OF THE INVENTION

The subject matter of the invention is a bone cement applicator for storage, mixing, and application of bone cement. The bone cement applicator is preferably implemented in the form of a closed prepack mixing system with an integrated extrusion device. The bone cement applicator is preferably well-suited and/or intended for arthroplasty, vertebroplasty, and kyphoplasty. Methods for the mixing and application of polymethylmethacrylate bone cement are proposed for this purpose as well.

It is the object of the invention to develop a bone cement applicator for storage, mixing, and application of polymethylmethacrylate bone cement by which the disadvantages of the prior art can be overcome. The bone cement powder and the monomer liquid are stored in separate compartments in the bone cement applicator before being mixed. The monomer transfer from the monomer liquid container into the bone cement powder takes place without the application of an externally provided vacuum. The mixing takes place appropriately in the closed device using a mixing rod with a mixer such that the medical user is not exposed directly to the bone cement powder or the monomer liquid. After the cement components are mixed, the step of removing the mixing rod from the mixing system by pulling out and/or breaking off the mixing rod is omitted. The bone cement thus produced can be manually extruded from the bone cement applicator without an external extrusion device having to be connected to the device.

It is therefore an object of the invention to develop a completely autonomous prepack mixing system that permits the cement components to be mixed and the mixed bone cement to be extruded without additional devices, such as external vacuum pumps and extrusion devices, being required.

The objects of the invention are met by a bone cement applicator for storage and mixing of a bone cement powder and a monomer liquid as well as for applying a pasty bone cement mixed together from the bone cement powder and the monomer liquid, the bone cement applicator comprising:

(A) a cartridge with a cylindrical internal space for mixing of the bone cement, whereby the cartridge comprises, on a front side, a cartridge head with a dispensing opening for expulsion of the bone cement from the internal space, and whereby the cartridge comprises a thread on a rear side situated opposite from the front side of the cartridge;

(B) a dispensing plunger for expelling the mixed bone cement from the internal space through the dispensing opening, whereby the bone cement powder is contained between the dispensing plunger and the cartridge head in the internal space of the cartridge;

(C) a threaded tube that is arranged at the rear side of the dispensing plunger that faces away from the cartridge head, whereby the threaded tube comprises a counter thread matching the thread on the rear side of the cartridge and the counter thread of the threaded tube engages the thread on the rear side of the cartridge, whereby the threaded tube projects out of the cartridge on the rear side of the cartridge, and whereby the dispensing plunger is arranged so as to be mobile in the internal space of the cartridge along the cylinder axis of the internal space in the direction of the cartridge head by screwing the threaded tube into or onto the cartridge;

(D) a receptacle, whereby a monomer liquid container is arranged on the inside of the receptacle, whereby the monomer liquid container contains the monomer liquid and can be opened on the inside of the receptacle, whereby the receptacle is plugged into the threaded tube on a rear side of the threaded tube that is opposite from the dispensing plunger, and is mobile in the threaded tube; and (E) a mixing rod, whereby the mixing rod with a mixer fastened to it is arranged in the internal space of the cartridge, whereby the mixer is fastened to a front side of the mixing rod that faces the cartridge head, whereby the mixing rod is connected, on a side opposite from the mixer, to a front side of the receptacle that faces the dispensing plunger, whereby the mixing rod is guided through a feedthrough in the dispensing plunger and is supported in the feedthrough so as to be axially mobile, such that the mixing rod with the mixer can be moved in the internal space for mixing of the bone cement powder with the monomer liquid by a motion of the receptacle against the cartridge, and whereby the mixing rod is connected to the receptacle so as to be detachable, and the mixing rod detached from the receptacle can be pushed into the receptacle when the receptacle is being propelled in the direction of the cartridge head.

Preferably, the receptacle is at least axially mobile in the threaded tube in the direction of the cylinder axis of the internal space of the cartridge. In this context, the receptacle preferably can be inserted, at least in sections thereof, into the threaded tube.

The receptacle is preferred to be an ampoule holder.

The invention can provide a part of the receptacle with the mixing rod, in particular a closure of the receptacle that faces the cartridge head, to detach from the remaining receptacle.

The internal space of the cartridge has a cylindrical geometry with a circular footprint. The cylindrical shape is the simplest shape by which the internal space of the cartridge can be implemented. A cylindrical shape shall be understood geometrically to mean the shape of a general cylinder of any footprint, i.e., not just a cylinder having a circular footprint. But the internal space of the cartridge needs to have a rotational symmetry, meaning a cylindrical shape with a circular footprint, because it would otherwise not be possible to screw the threaded tube in or to adequately seal the dispensing plunger with respect to the internal wall of the internal space. But the cylindrical space of the threaded tube can be realized by a cylinder jacket of a cylinder of any footprint, including non-circular or non-round footprints, because the receptacle is simply to be pushed into the space. However, according to the invention, a cylindrical geometry with a rotationally symmetrical and, in particular, circular footprint is preferred also for the space of the threaded tube, because this geometry is the easiest to manufacture. The same principle applies to the inside of the receptacle, which is also preferred to be cylinder-shaped.

Preferably, the monomer liquid container is an ampoule made of glass or a plastic material. An ampoule made of glass or plastic can be opened particularly reliably. Moreover, the monomer liquid can be stored in the ampoule as a monomer liquid container for particularly long periods of time. Alternative monomer liquid containers can be, for example, coated film bags.

The receptacle is preferably designed as an ampoule holder. It is particularly preferred in this context for the ampoule holder to be suitable and provided for holding an ampoule made of glass or plastic.

The invention can preferably provide the dispensing opening for storage and mixing to be closed by a closure that can be opened. This configuration provides a closed prepack mixing system.

In this context, the invention can provide the closure to be connected to the cartridge head in a detachable manner by a thread or a bayonet closure.

The invention can provide the closure to close the dispensing opening in a liquid-tight manner or in a gas-tight and liquid-tight manner.

This configuration ensures that no bone cement powder, no monomer liquid, and no bone cement can leak from the internal space of the cartridge while the bone cement is being mixed.

With the exception of the starting components, the monomer liquid container, and any seals that may be present, all parts of the bone cement applicator preferably consist of plastic, in particular a thermoplastic material. If the monomer liquid container consists of a plastic material, it needs to consist of a brittle breakable plastic material. The seals preferably consist of silicon or rubber.

The invention can provide the thread on the rear side of the cartridge to be an internal thread and the counter thread on the threaded tube to be an external thread, such that the dispensing plunger can be moved in the internal space of the cartridge axially along the cylinder axis of the internal space in the direction of the cartridge head by screwing the threaded tube into the internal space of the cartridge.

Alternatively, the thread on the rear side of the cartridge can just as well be an external thread and the threaded tube can have an internal thread and be screwed onto the cartridge in the way of a sleeve. For this purpose, the threaded tube can be designed to have an external tube with the internal thread and an internal tube, whereby only the internal tube of the threaded tube extends into the inside of the cartridge. The internal tube then needs to have no thread. The threaded tube is then a double-walled tube with an external thread, whereby the two tube walls are connected to each other on a rear side that is situated opposite from the cartridge head.

If the thread on the rear side of the cartridge is an internal thread and the counter thread on the threaded tube is an external thread, the bone cement applicator can be designed to be particularly compact and simple. The threaded tube with an external thread is then a simple tube, whereas it would need to be designed to be two-part if it has an internal thread, namely with an external tube and, on the inside, with struts or another tube by which the dispensing plunger is driven and in which the receptacle is guided so as to be axially mobile.

Moreover, the threaded tube can comprise a cylindrical space that is open on the rear side of the threaded tube, whereby the receptacle is plugged into the cylindrical space of the threaded tube from the rear side of the threaded tube.

The receptacle can thus be guided in the cylindrical space of the threaded tube. Moreover, the monomer liquid can be conducted and/or flow from the receptacle into the cylindrical space and, from there, into the internal space of the cartridge, whereby the cylindrical space is closed on its rear side by the receptacle that is inserted into the cylindrical space.

In this context, the receptacle can be sealed with respect to the cylindrical space of the threaded tube, whereby the receptacle is supported so as to slide in the threaded tube.

By this design, the monomer liquid can be conducted through the cylindrical space without possibly leaking outwards.

Alternatively, the threaded tube can comprise, on its rear side, a cylindrical feedthrough that is sealed with respect to the receptacle, whereby the receptacle is supported so as to slide in the feedthrough.

As before, by this design, the monomer liquid can be conducted through the cylindrical space without possibly leaking outwards.

Moreover, the mixing rod can be detached from the receptacle by pressing onto the mixer touching against the cartridge head, and/or by rotating or screwing the threaded tube with the receptacle against the mixer, which is secured against rotation in the internal space.

By this design, the mixing rod can be detached from the receptacle by moving the receptacle against the mixer, which is affixed in the area of the cartridge head. There is then no need to have a separate device for detachment of the mixing rod from the receptacle. This simplifies the design of the bone cement applicator.

The invention can just as well provide the dispensing plunger and the threaded tube to be one and the same part, whereby the threaded tube is closed off by the dispensing plunger at its front side, which faces the cartridge head.

The one-part design of threaded tube and dispensing plunger allows the design to be inexpensive and, in addition, the bone cement applicator can be assembled more easily. Moreover, no monomer liquid can leak at the sites at which the threaded tube and the dispensing plunger are connected.

Preferably, the invention can provide the dispensing plunger not to be movable within the internal space through a motion of the mixing rod through the feedthrough in the dispensing plunger.

This configuration ensures that the mixer can reach all areas of the internal space of the cartridge and that, thus, good mixing of the bone cement can be attained.

Moreover, the dispensing plunger can include at least one channel that is impermeable to the bone cement powder and is permeable to the monomer liquid and gases.

By this design, the monomer liquid can flow through the dispensing plunger to the bone cement powder without the bone cement powder having to move in the direction of the monomer liquid container. This configuration ensures that the bone cement is produced only in the internal space of the cartridge between the dispensing plunger and the cartridge head.

Moreover, according to the invention, the receptacle can be pushed into the threaded tube up to a limit stop, whereby the mixing rod is not detachable from the receptacle upon a motion of the receptacle up to the limit stop and the mixing rod is detachable from the receptacle by screwing the threaded tube into or onto the cartridge.

By this design, the bone cement applicator can be operated easily. What this also attains is that the mixing rod is not already detached from the receptacle while the bone cement is being mixed, but only when the receptacle is screwed to the threaded tube.

According to a preferred development of the present invention, a connection, in particular a fixation cap, can be provided through which the receptacle can be affixed to the threaded tube, whereby the connection preferably is connected, via a rear internal thread with a smaller diameter than the thread of the threaded tube, to an external thread of a sleeve of an opening facility, whereby the sleeve can be pushed onto the monomer liquid container on the inside of the receptacle in order to open the monomer liquid container, and whereby the fixation cap comprises a front internal thread that matches the thread of the threaded tube.

By this design, the receptacle can be connected to the threaded tube, preferably through the aid of the extant opening facility, and, in the process, the mixing rod can be detached from the receptacle, which simplifies the design of the bone cement applicator and improves its ease-of-use.

According to a preferred development, the present invention can provide an opening facility, which can be operated from outside and can be used to open the monomer liquid container on the inside of the receptacle, to be arranged on the receptacle.

By this design, the monomer liquid container can be opened from outside, but simultaneously inside the receptacle. This prevents the user from being exposed to the monomer liquid and prevents the monomer liquid that is intended and needed for the production of a bone cement from getting lost.

Moreover, the monomer liquid container can be opened by inserting or screwing the opening facility into the receptacle, whereby the monomer liquid container is situated on the inside of the receptacle.

By this design, the entire bone cement applicator can be operated by pushing and/or screwing-in its parts, namely the opening facility into the receptacle and the receptacle with the threaded tube and the threaded tube into the cartridge. By this design, the bone cement applicator is particularly easy to use.

In this context, the monomer liquid container can be an ampoule made of glass or a plastic material, whereby the ampoule comprises an ampoule head, a cylindrical ampoule body, and an ampoule base situated opposite from the ampoule head, whereby the ampoule head has a smaller diameter than the ampoule body and is connected to the ampoule body by shoulders, whereby the opening facility comprises a sleeve that pushes onto the shoulders of the ampoule during the insertion or screwing-in.

The sleeve is preferably implemented in the form of a hollow cylinder, whereby an opening for gas exchange can be provided in order to prevent any overpressure in the bone cement applicator.

A uniform pressure can be exerted onto the ampoule by the sleeve and reproducible opening of the ampoule can thus be attained.

Because the opening facility comprises a sleeve that pushes onto the shoulders of the ampoule during the insertion and/or screwing-in, the ampoule base is pushed onto a projection on the inside of the receptacle and the ampoule is thus opened at the ampoule base allowing the monomer liquid to flow out.

In this context, the sleeve of the opening facility can project out of the receptacle on the side opposite from the cartridge head, whereby the sleeve preferably projects sufficiently far out of the receptacle such that fully inserting or screwing the sleeve into the receptacle is assured to fracture the ampoule.

By this design, the sleeve can be pushed particularly easily into the receptacle and the ampoule can thus be opened.

Moreover, the invention can provide a fixation cap of the opening facility to comprise an external thread and the receptacle to comprise a matching rear-side internal thread, and the fixation cap to form a limit stop for the receptacle.

This design allows a particularly compact bone cement applicator to be provided that can be operated easily and reliably.

The invention can just as well provide at least one gas supply opening in the wall of the receptacle that connects the inside of the receptacle to the surroundings of the bone cement applicator, whereby the at least one gas supply opening can be closed by inserting or screwing-in the opening facility, in particular can be closed by inserting or screwing-in the sleeve.

Using the gas supply openings, the inside of the receptacle and, through a connection, the internal space of the cartridge as well and the inside of the threaded tube and/or the cylindrical space of the threaded tube of the bone cement applicator can be sterilized with a sterilizing gas, such as ethylene oxide. Concurrently, the gas supply opening is closed by the sleeve before the monomer liquid container is opened such that no monomer liquid can leak towards outside through the gas supply openings.

Moreover, the inside of the receptacle can be connected in a liquid-permeable manner to an internal space of the cartridge, whereby, preferably, the front side of the receptacle facing the cartridge head comprises at least one liquid-permeable passage, and the dispensing plunger comprises at least one liquid-permeable channel for this purpose.

Upon appropriate positioning of the bone cement applicator, namely with the cartridge head facing downward, this ensures that the monomer liquid can readily flow out of the receptacle into the threaded tube and out of the threaded tube into the internal space of the cartridge between the dispensing plunger and the cartridge head.

Preferably, the inside of the receptacle is connected to the internal space of the cartridge in a liquid-permeable manner, but impermeable to the bone cement powder, whereby the dispensing plunger particularly preferably comprises at least one liquid-permeable and bone cement powder-impermeable channel. For this purpose, it is preferred to have a pore disk arranged on or in the dispensing plunger.

Preferably, the invention can just as well provide the cartridge head to be a cartridge lid that can be screwed onto the cartridge, whereby the cartridge lid seals the internal space of the cartridge at the front side thereof in a gas-tight and liquid-tight manner, and whereby the dispensing opening is arranged in the cartridge lid, preferably is arranged in a socket in the cartridge lid.

This configuration allows the bone cement applicator to be assembled particularly easily and inexpensively. Accordingly, other parts of the bone cement applicator can be inserted into the otherwise cylindrical cartridge before the cartridge head closes off the cartridge.

According to a preferred development, the invention can provide a mandrel for opening of the monomer liquid container to be arranged on the side of the receptacle that points into the inside of the receptacle.

By this design, the monomer liquid container can be opened at a defined place inside the receptacle.

In this context, the mixing rod can extend all the way into the mandrel and the mixing rod can push through the mandrel, when the mixing rod detaches from the receptacle, or the mandrel can be an extension of the mixing rod and the mandrel can separate from the receptacle as well when the mixing rod detaches from the receptacle.

These two measures allow the mixing rod to be pushed reliably into the receptacle while the bone cement is being dispensed from the internal space of the cartridge, without the mixing rod becoming lodged in the receptacle while this is ongoing, such as, for example, on fragments of the opened monomer liquid container.

Accordingly, the invention can provide the mixing rod in the receptacle to be appropriately arranged within a mandrel that points into the inside of the receptacle such that the mixing rod can be pushed through the mandrel into the inside of the receptacle.

By this design, the mixing rod is pushed in a targeted manner through the opening in the monomer liquid container produced by the mandrel and into the monomer liquid container. For this purpose, the mixing rod is preferably manufactured from a harder material than the mandrel and the receptacle. For example, the mixing rod can consist of metal and the mandrel with the receptacle can consist of a plastic material.

The mixing rod can comprise, in its connection to the receptacle, a circular disk with an external thread, whereby the circular disk is screwed into a matching internal thread on the front side of the receptacle that faces the cartridge head, whereby the external thread of the circular disk and the internal thread on the front side of the receptacle are preferred to be left-hand threads.

By this design, the mixing rod with the circular disk can be separated from the front side of the receptacle through a left-hand turn, and the mixing rod with the circular disk can be pushed into the inside of the receptacle, when the threaded tube with the receptacle is screwed into the cartridge.

The objects underlying the present invention are also solved by a method for the production of a bone cement using a bone cement applicator according to the invention, comprising the following steps of:

(A) opening the monomer liquid container on the inside of the receptacle, and the monomer liquid flowing out of the monomer liquid container, whereby the monomer liquid flows out of the receptacle into the bone cement powder in the internal space of the cartridge;

(B) alternating pulling and pushing the receptacle out of and into the threaded tube, whereby the mixing rod, which is fastened to the front side of the receptacle in a detachable manner, is moved through the feedthrough in the dispensing plunger, whereby that motion moves the mixer in the internal space of the cartridge and thus the bone cement powder and the monomer liquid are mixed together to form the bone cement;

(C) detaching the mixing rod from the receptacle by screwing the threaded tube with the receptacle onto or into the internal space of the cartridge;

(D) opening the dispensing opening; and (E) extruding the bone cement out of the internal space of the cartridge through the opened dispensing opening, whereby the bone cement is extruded out of the internal space of the cartridge by the dispensing plunger and the dispensing plunger is driven by screwing the threaded tube onto the cartridge or by screwing the threaded tube into the cartridge, and whereby the mixing rod is pushed into the receptacle when the threaded tube is screwed on or in.

Referring to bone cements with a lower viscosity, the receptacle can first be pulled out of the threaded tube and, therefore, the mixer can initially be pulled away from the cartridge head in the direction of the rear side of the internal space of the cartridge. Referring to bone cements with a higher viscosity, the receptacle needs to be pushed into the threaded tube initially and, in the process, the mixer needs to be pushed initially from the rear side in the direction of the cartridge head. This prevents a stable gel layer from being generated at the junction as a reaction product of the bone cement powder and the monomer liquid, when the monomer liquid is supplied, which can no longer be penetrated by the supply of more monomer liquid.

The dispensing plunger can be firmly connected to a front side of the threaded tube that faces the cartridge head.

In this context, the dispensing plunger can comprise at least one channel that is impermeable to the bone cement powder and is permeable to the monomer liquid and gases, whereby the monomer liquid flows through the dispensing plunger into the internal space of the cartridge in step (A), and the dispensing plunger is pushed in the direction of the cartridge head in step (E) by the threaded tube being screwed into the cartridge or the threaded tube being screwed onto the cartridge.

This renders the design of the bone cement applicator inexpensive and simplifies the production method.

In this context, the invention can provide a gas contained in the bone cement in step (E) to be extruded from the bone cement through the at least one channel in the dispensing plunger, when the threaded tube is being pushed into or screwed onto or screwed into the internal space of the cartridge.

By this design, the bone cement is degassed during extrusion through the dispensing plunger.

Moreover, the invention can prevent the monomer liquid container from being opened in step (A) by pushing or screwing an opening facility into the receptacle.

This makes the method particularly easy for the user to implement. Moreover, a defined force for opening of the monomer liquid container can be provided, and reproducible opening of the monomer liquid container can thus be attained.

In this context, the invention can provide the monomer liquid container in step (A) to be pushed onto a mandrel on the inside of the receptacle and the receptacle to thus be opened, whereby the monomer liquid container preferably is an ampoule made of glass or a plastic material and the ampoule is opened by the mandrel at an ampoule base of the ampoule.

This also serves for opening the monomer liquid container at a defined place and to thus render the process of opening the monomer liquid container reproducible.

In this context, the mandrel can be pushed into the receptacle by the mixing rod or the mixing rod can puncture the mandrel and can be pushed through the mandrel into the receptacle in step (E).

This ensures that the mixing rod can be pushed without resistance through the opened monomer liquid container or through its fragments into the receptacle and into the opened monomer liquid container.

Moreover, the receptacle can be moved linearly in step (B), and the receptacle can be fastened to the threaded tube after step (B) and before step (C), whereby the receptacle is preferably fastened to the threaded tube by the thread of the threaded tube, and the receptacle fastened to the threaded tube can be screwed into the cartridge in steps (C) and (E).

This can prevent the mixing rod from being detached from the receptacle during the mixing process. Moreover, it prevents a large force from being exerted on the closure of the dispensing opening during the mixing process, and prevents bone cement from exiting from the cartridge already before the mixing process is completed. Moreover, the bone cement can be forcefully expelled from the internal space of the cartridge process by the screw-type process, and the mixing rod can be detached from the receptacle through the aid of the force from the receptacle being screwed into the cartridge.

The invention can just as well provide the inside of the receptacle to be connected in a gas-permeable manner to the surroundings of the bone cement applicator before step (A), whereby the inside of the receptacle is closed before step (A) or during step (A), while the monomer liquid container is being opened.

This allows the inside of the receptacle and the internal space of the cartridge, i.e., the entire bone cement applicator including its contents, to be sterilized by a sterilizing gas, such as ethylene oxide. Concurrently, the monomer liquid cannot exit from the receptacle once the monomer liquid container has been opened inside the receptacle.

The bone cement applicator can be held or set up with the cartridge head facing downwards before step (A), whereby the cartridge head preferably stays oriented downwards during steps (A) and (B) such that the monomer liquid flows into the internal space of the cartridge driven by gravity.

By this orientation, no additional pump is required in order to transfer the monomer liquid into the internal space of the cartridge to the bone cement powder.

Moreover, the invention can provide any still remaining part of the monomer liquid to be pushed into the internal space of the cartridge during the insertion of the receptacle into the threaded tube during step (B).

What this attains is that the monomer liquid is transferred as completely as possible into the bone cement powder in order to attain the desired mixing ratio of bone cement powder and monomer liquid and to thus generate a bone cement with the desired properties.

Lastly, the invention can just as well provide the receptacle to be inserted fully into the threaded tube before step (C) and the mixer to thus touch against the cartridge head in the internal space of the cartridge, whereby the mixing rod is detached from the receptacle in step (C) and is pushed into the receptacle in step (E) by the threaded tube with the receptacle being screwed onto or into the cartridge.

By this feature, the mixing rod can be detached from the receptacle in a simple and forceful manner.

The invention is based on finding, surprisingly, that providing a mixing rod that can be detached from the receptacle and a mixing rod that can be retracted into the receptacle allows a bone cement applicator to be provided, in which the mixing rod does not need to be pulled out of the bone cement applicator and in which the mixing rod does not need to be broken off and removed, when the bone cement is dispensed with the bone cement applicator. Surprisingly, the receptacle, in which the monomer liquid container is arranged, can be used to accommodate the mixing rod. As a result, the mixing rod does not impede the motion of the dispensing plunger during extrusion of the bone cement. Moreover, a space on the inside of the threaded tube is provided, in which the receptacle can be moved independent of the cartridge, whereby the mixer is concurrently operated manually through the motion of the receptacle in the internal space of the cartridge for mixing of the bone cement.

Once the monomer liquid container is opened, the mixing rod is pushed into the hollow monomer liquid container inside the receptacle that has been emptied of monomer liquid, because the mixing rod and the monomer liquid container are arranged in succession in the bone cement applicator. The bone cement applicator according to the invention is a prepack mixing system and can be operated without prior assembly steps. No external vacuum source is required for the monomer transfer. The dispensation of the bone cement takes place through a manual screw motion of the threaded tube with the hollow cylinder-shaped receptacle affixed to it, whereby the threaded tube forms the dispensing plunger on its front side that faces the cartridge head or drives the dispensing plunger in the internal space of the cartridge. The screw motion develops a sufficient extrusion force to be able to extrude even a high viscosity bone cement out of the cartridge and also for detaching the mixing rod from the receptacle. The components of the bone cement applicator can essentially be produced by plastic injection molding and preferably consist of inexpensive thermoplastic material. The O-rings consist of elastomers that are common in medical technology, such as silicone or EPDM (terpolymers of ethylene, propylene, and a diene).

An exemplary bone cement applicator according to the invention designed for storage, mixing, and application, is composed of:

(a) a hollow cylinder-shaped cartridge, whereby a fastener for a cartridge lid (as a cartridge head) is arranged on a front end of the cartridge, and whereby an internal thread is arranged on the internal wall of the cartridge on the opposite rear-side end of the cartridge;

(b) a cartridge lid to be connected by the fastener to the front end of the cartridge in a gas-tight and liquid-tight manner, whereby the cartridge lid possesses a dispensing opening;

(c) a closure stopper that is arranged in the dispensing opening of the cartridge lid in a gas-tight and detachable manner;

(d) an ampoule holder, at least sections of which are hollow and cylinder-shaped, as a receptacle that comprises an internal thread at least in a rear section thereof;

(e) a closure on the front side of the ampoule holder that closes the hollow and cylinder-shaped ampoule holder on a longitudinal side, whereby a mixing rod with a mixer is attached in a detachable manner on the side of the closure that faces the cartridge head, and whereby the opposite side of the closure is connected to a mandrel;

(f) a threaded tube, whose front side forms a dispensing plunger that can be axially shifted in the cartridge, whereby the threaded tube has an external thread that is screwed into the internal thread on the rear-side end of the cartridge, whereby the dispensing plunger is permeable to gases and liquids and is impermeable to bone cement powder particles, and is arranged between the mixer and the closure of the ampoule holder in the cartridge;

(g) a monomer liquid container containing monomer liquid whose base side is arranged at a distance above the mandrel in the ampoule holder;

(h) a shiftable sleeve as part of an opening facility that is arranged appropriately above the monomer liquid container in the hollow and cylinder-shaped ampoule holder so as to be shifted axially, such that the sleeve projects beyond the edge of the hollow and cylinder-shaped ampoule holder, whereby the sleeve has an external thread by which the sleeve is screwed into the internal thread of the ampoule holder;

(i) a fixation cap that is screwed onto the external thread of the hollow cylinder-shaped ampoule holder by a first rear internal thread and that can be screwed onto the external thread of the threaded tube by a second front internal thread that has a larger diameter than the first internal thread;

(j) optionally, at least one ventilation opening in the jacket surface of the hollow and cylinder-shaped ampoule holder, whereby the ventilation opening can be closed in a gas-tight manner by shifting the sleeve axially;

(k) a bone cement powder that is arranged in an internal space of the cartridge that is formed by the internal wall of the cartridge, the cartridge lid, and the dispensing plunger;

(l) whereby the hollow and cylinder-shaped ampoule holder is inserted into the open end of the threaded tube that is opposite from the dispensing plunger, such that the ampoule holder is axially mobile in the threaded tube; and (m) at least the mixing rod can be shifted into the hollow space of the ampoule holder or of the monomer liquid container after the monomer liquid container has been opened.

It is advantageous to have the closure with the mixing rod and the mandrel be designed as a single part. This clearly reduces the assembly effort as compared to a two-part or three-part closure with mixing rod and mandrel. The one-part closure with mixing rod and mandrel can advantageously be manufactured by plastic injection molding.

The invention can just as well provide the closure to be affixed in a detachable manner in the hollow and cylinder-shaped ampoule holder through a press-fit. In this context, the closure can be conical and can be supported in a conical seat of the hollow and cylinder-shaped ampoule holder. The cone of the closure tapers in the direction of the cartridge head. Upon a motion of the hollow and cylinder-shaped ampoule holder in the direction of the cartridge head, the mixing rod with mixing elements braces on the internal side of the cartridge lid and pushes the conical closure out of its seat. The mandrel with the closure and the mixing rod then enter the inside of the ampoule holder and the opened monomer liquid container.

In another implementation variant, an internal part of the closure in the hollow and cylinder-shaped ampoule holder has an external thread that is screwed into an internal thread of the hollow and cylinder-shaped ampoule holder, whereby the internal part of the closure preferably possesses a left-hand external thread. When the hollow and cylinder-shaped ampoule holder is rotated, it moves in the direction of the cartridge head. The mixing rod with the mixing elements is pressed to the inside of the lid. With increasing contact pressure against the lid, the mixing rod can no longer rotate along with the ampoule holder. The internal part of the closure is then rotated out of the internal thread of the hollow and cylinder-shaped ampoule holder. The internal part of the closure leaves its seat in the hollow and cylinder-shaped ampoule holder and is pushed, together with the mandrel and the mixing rod, into the opened monomer liquid container.

In another implementation variant, the mixing rod is pressed into the closure and penetrates through the closure and the mandrel after the monomer liquid container has been opened. Then, the mixing rod is inserted into the ampoule holder.

The invention can just as well provide the hollow and cylinder-shaped ampoule holder to have a diameter at its cylinder-shaped head side that is equal to or smaller than the internal diameter of the hollow cylinder-shaped cartridge, and can provide the hollow and cylinder-shaped ampoule holder to be axially movable in the cartridge by its head side in a gas-tight manner.

The sleeve can be designed as a hollow cylinder, whereby the cylinder jacket of the sleeve rests on the monomer liquid container.

Moreover, the invention can provide the internal part of the closure to have an external diameter that is smaller than the internal diameter of the monomer liquid container. By this design, the internal part of the closure with the mandrel and the mixing rod can be readily pushed into the inside of the opened monomer liquid container.

An exemplary method according to the invention for the mixing and application of polymethylmethacrylate bone cement using a bone cement applicator according to the invention can be implemented through the following steps proceeding in the order given:

(a) positioning the bone cement applicator vertically with the cartridge head downwards;

(b) screwing the opening facility in the direction of the cartridge head;

(c) shifting the sleeve in the direction of the cartridge head;

(d) optionally, closing the at least one gas supply opening in the hollow and cylinder-shaped ampoule holder using the sleeve;

(e) shifting the monomer liquid container in the direction of the mandrel by shifting the sleeve axially;

(f) destroying the base of the monomer liquid container by the mandrel;

(g) flowing monomer liquid out through the closure and the dispensing plunger, which is permeable to gases and liquids, into the internal space of the cartridge to the bone cement powder;

(h) retracting the hollow and cylinder-shaped ampoule holder in the threaded tube opposite to the cartridge head during a concurrent backward motion of the mixing rod while mixing the bone cement powder and the monomer liquid;

(i) moving the ampoule holder forward in the threaded tube, transferring the remaining monomer liquid, through the overpressure over the monomer liquid, through the closure and the dispensing plunger, which is permeable to gases and liquids, during a concurrent backward motion of the mixing rod while mixing the bone cement powder and the monomer liquid;

(j) multiply repeating steps (h) and (i) to produce the bone cement from the mixture of polymethylmethacrylate bone cement powder and monomer liquid;

(k) fastening the receptacle to the threaded tube by screwing the fixation cap onto the threaded tube;

(l) removing the closure stopper from the dispensing opening;

(m) screwing the threaded tube in the cartridge in the direction of the cartridge head, whereby the mixing rod with the mixing elements lands on the internal side of the lid (of the cartridge head) and pushes the internal part of the closure out of its conical seat in the hollow and cylinder-shaped ampoule holder in the direction of the cartridge base;

(n) inserting the closure with the mandrel and mixing rod into the opened monomer liquid container; and (o) extruding the polymethylmethacrylate bone cement in the direction of the cartridge head through the screw motion of the threaded tube.

An exemplary alternative method for the mixing and application of polymethylmethacrylate bone cement using the bone cement applicator according to the invention can be characterized by the following steps proceeding in the order given:

(a) positioning the bone cement applicator vertically with the cartridge head downwards;

(b) screwing the fixation cap, which is screwed onto the hollow and cylinder-shaped ampoule holder as the receptacle, in the direction of the cartridge head;

(c) shifting the sleeve in the direction of the cartridge head using the fixation cap;

(d) closing the at least one gas supply opening in the hollow and cylinder-shaped ampoule holder using the sleeve;

(e) shifting the monomer liquid container in the direction of the mandrel by shifting the sleeve axially;

(f) destroying the base of the monomer liquid container by the mandrel;

(g) flowing monomer liquid out through the closure and the dispensing plunger, which is permeable to gases and liquids, into the front part of the internal space of the cartridge to the bone cement powder;

(h) retracting the hollow and cylinder-shaped ampoule holder in the threaded tube opposite to the cartridge head during a concurrent backward motion of the mixing rod while mixing the bone cement powder and the monomer liquid;

(i) moving the ampoule holder forward in the threaded tube, transferring the remaining monomer liquid, through the overpressure over the monomer liquid, through the closure and the dispensing plunger, which is permeable to gases and liquids, during concurrent backward motion of the mixing rod while mixing the bone cement powder and the monomer liquid;

(j) multiply repeating steps (h) and (i) to produce the bone cement from the mixture of polymethylmethacrylate bone cement powder and monomer liquid;

(k) fastening the receptacle to the threaded tube by screwing the fixation cap onto the threaded tube;

(l) removing the closure stopper from the dispensing opening;

(m) screwing the threaded tube in the cartridge in the direction of the cartridge head, whereby the mixing rod with the mixing elements lands on the internal side of the lid and unscrews the external thread of the internal part of the closure from the internal thread of the hollow and cylinder-shaped ampoule holder in the direction of the cartridge base;

(n) inserting the closure with mandrel and mixing rod into the opened monomer liquid container; and (o) extruding the polymethylmethacrylate bone cement in the direction of the cartridge head through the screw motion of the threaded tube.

Another exemplary alternative method for the mixing and application of polymethylmethacrylate bone cement using the bone cement applicator according to the invention can be characterized by the following steps proceeding in the order given:

(a) positioning the bone cement applicator vertically with the cartridge head downwards;

(b) screwing the fixation cap, which is screwed onto the hollow and cylinder-shaped receptacle, in the direction of the cartridge head;

(c) shifting the sleeve in the direction of the cartridge head using the fixation cap;

(d) closing the at least one gas supply opening in the hollow and cylinder-shaped receptacle using the sleeve;

(e) shifting the monomer liquid container in the direction of the mandrel by shifting the sleeve axially;

(f) destroying the base of the monomer liquid container by the mandrel;

(g) flowing monomer liquid out through the closure and the dispensing plunger, which is permeable to gases and liquids, into the front part of the internal space of the cartridge to the bone cement powder;

(h) retracting the hollow and cylinder-shaped receptacle in the threaded tube opposite to the cartridge head during a concurrent backward motion of the mixing rod while mixing the bone cement powder and the monomer liquid;

(i) moving the receptacle forward in the threaded tube, transferring the remaining monomer liquid, through the overpressure over the monomer liquid, through the closure and the dispensing plunger, which is permeable to gases and liquids, during concurrent backward motion of the mixing rod while mixing the bone cement powder and the monomer liquid;

(j) multiply repeating steps (h) and (i) to produce the bone cement from the mixture of polymethylmethacrylate bone cement powder and monomer liquid;

(k) fastening the receptacle to the threaded tube by screwing the fixation cap onto the threaded tube;

(l) removing the closure stopper from the dispensing opening;

(m) screwing the threaded tube in the cartridge in the direction of the cartridge head, whereby the mixing rod with the mixing elements lands on the internal side of the lid and punctures the closure and the mandrel;

(n) inserting the mixing rod into the opened monomer liquid container; and (o) extruding the polymethylmethacrylate bone cement in the direction of the cartridge head through the screw motion of the threaded tube.

The extrusion of the bone cement takes place by propelling the dispensing plunger via the threaded tube, whereby the ampoule holder is affixed to the threaded tube.

BRIEF DESCRIPTION OF THE DRAWING

The disclosure is best understood from the following detailed description when read in connection with the accompanying drawing. Further exemplary embodiments of the invention are explained below with reference to eight schematic figures, although without limiting the scope of the invention. In the figures.

DETAILED DESCRIPTION OF THE DISCLOSURE

Figure 1:
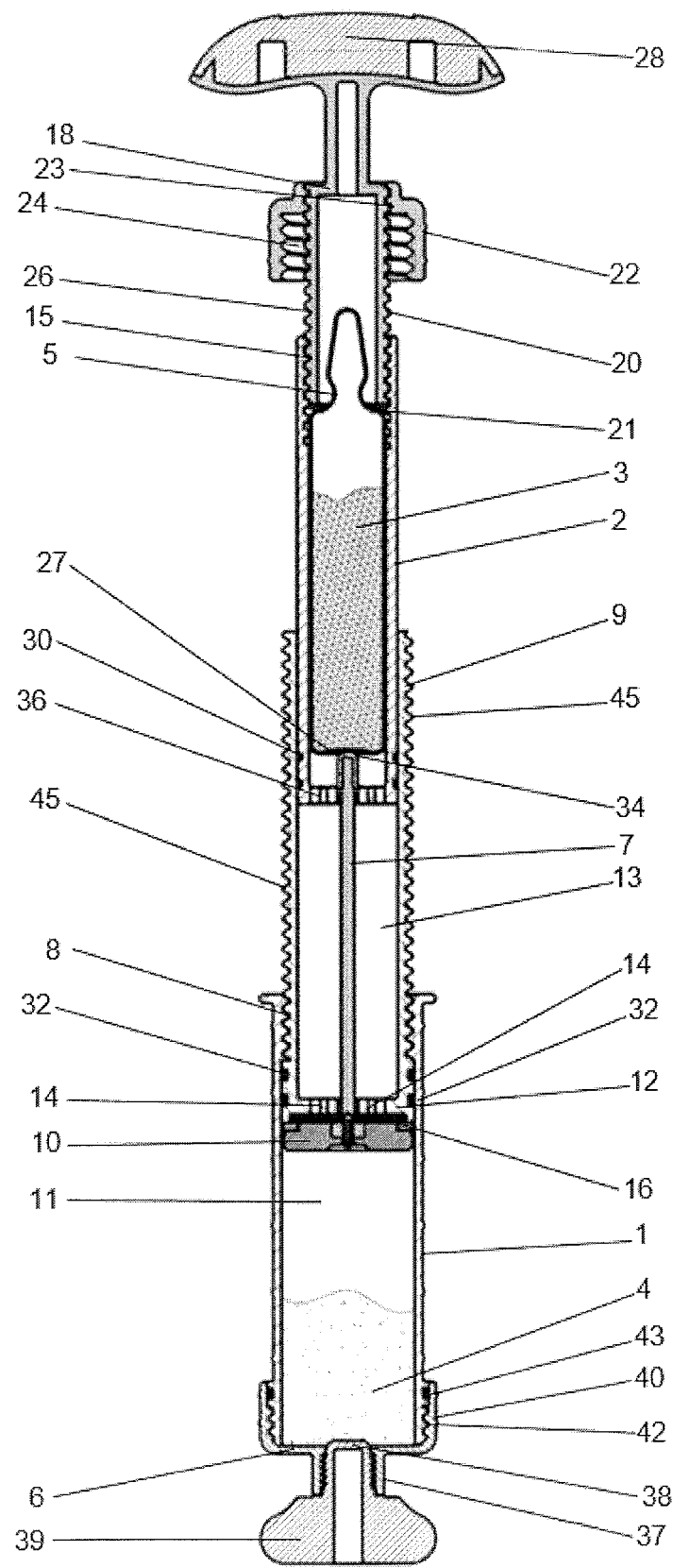
FIG. 1 shows a schematic cross-sectional view of an exemplary bone cement applicator according to the invention for the production of a bone cement dough.
Figure 2:
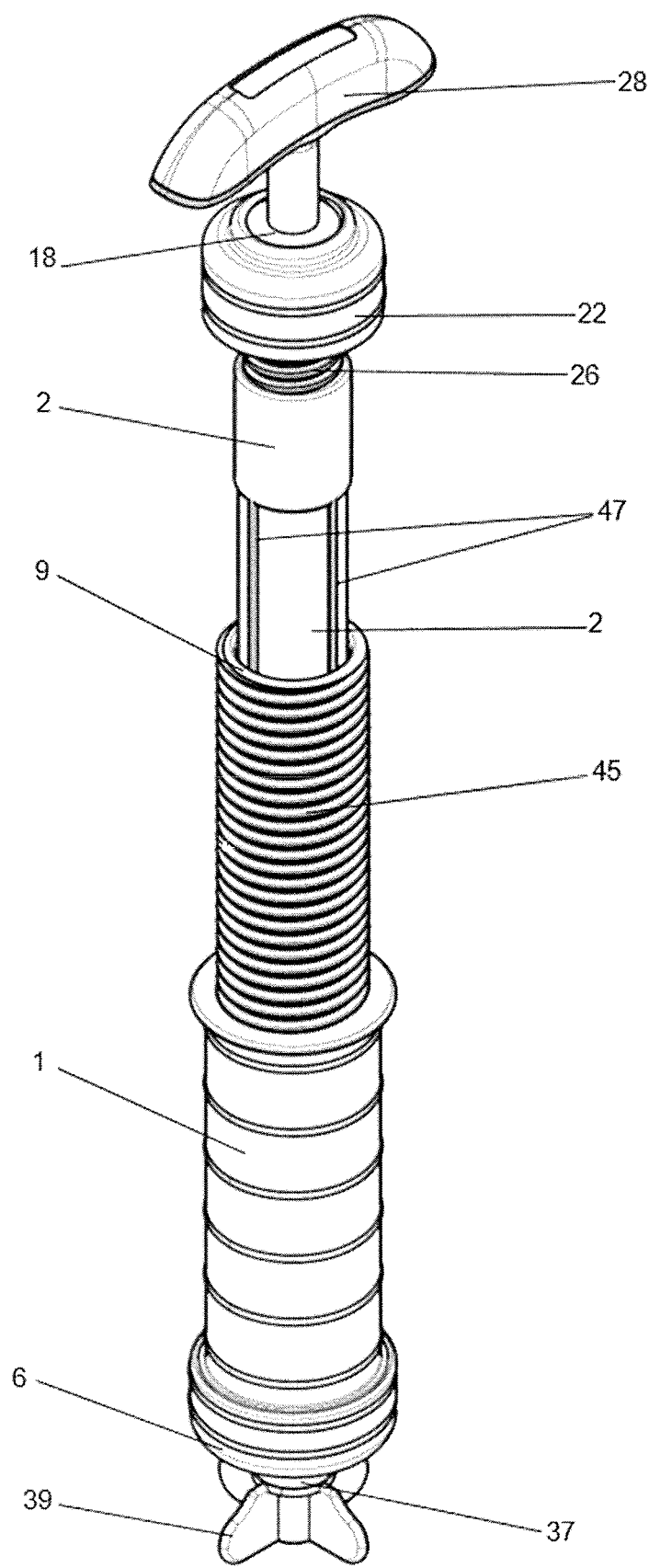
FIG. 2 shows a schematic perspective external view of the bone cement applicator according to FIG. 1.
Figure 3:
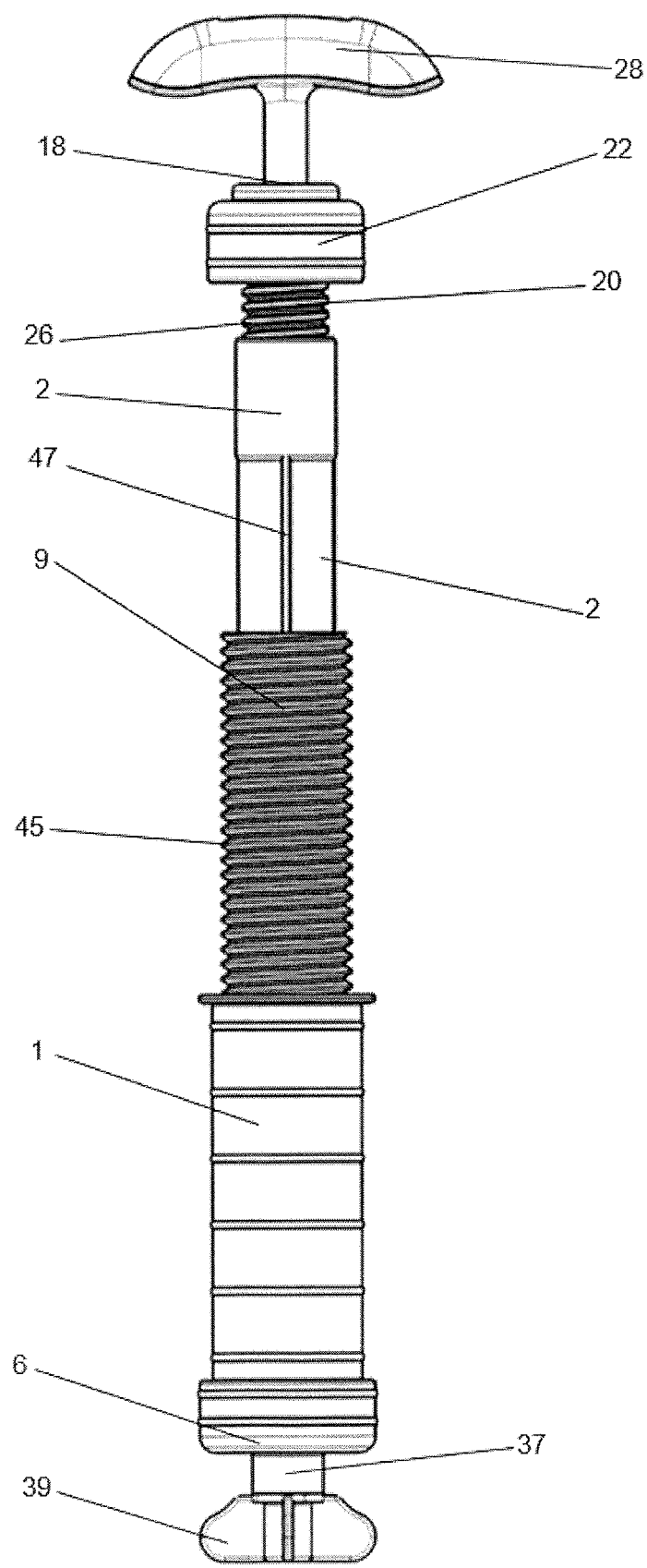
FIG. 3 shows a schematic side view of the bone cement applicator according to FIGS. 1 and 2.

The figures show depictions of a bone cement applicator according to the invention for the storage of starting components 3, 4 of a bone cement 48 and for the mixing of the bone cement 48. In this context, FIGS. 1 and 4 to 7 show the work-flow of a method according to the invention that is implemented using the bone cement applicator according to the invention in the form of five cross-sectional views of the bone cement applicator.

The bone cement applicator according to the invention comprises a tube-shaped cartridge 1 made of plastic that forms a front part (on the bottom in FIGS. 1 to 8) of the bone cement applicator. A rear-side rear part of the bone cement applicator is formed by a receptacle 2. The bone cement applicator is intended for the production of a bone cement 48 (see FIGS. 5 to 7) that is produced from a monomer liquid 3 and from a bone cement powder 4. The monomer liquid 3 and the bone cement powder 4 are the starting components 3, 4 of the bone cement 48. The monomer liquid 3 is contained in an ampoule 5 that can be fractured and is made of glass or a plastic material as the monomer liquid container for the monomer liquid 3, whereby the ampoule 5 is plugged into the receptacle 2. The cartridge 1 forms a cylindrical internal space 11 on its inside that contains the bone cement powder 4. Accordingly, the bone cement applicator is also well-suited for storage of the monomer liquid 3 and the bone cement powder 4.

The cartridge 1 comprises a cartridge lid 6 as a cartridge head on its front side (on the bottom in the figures). A dispensing opening is provided in the cartridge lid 6. According to an alternative variant of the bone cement applicator, multiple gas supply openings (not shown) through which a gas can be aspirated from the inside of the bone cement applicator and through which a sterilizing gas such as ethylene oxide can be delivered for sterilization of the inside of the bone cement applicator can be situated in the side wall of the receptacle 2.

A mixing rod 7 is fastened to the front side of the receptacle 2 and extends from the front side of the receptacle 2 up into the front part of the cartridge 1, in which the bone cement powder 4 is situated.

An internal thread 8 is situated on the rear-side end of the cartridge 1. A threaded tube 9 with a matching external thread 45 is screwed into the internal thread 8. The threaded tube 9 is closed on its front side (on the bottom in the figures) by a dispensing plunger 12. A cylindrical space 13 is formed on the inside of the threaded tube 9 and is bordered on its front side by the dispensing plunger 12 and has the receptacle plugged into it so as to be axially mobile.

The receptacle 2 comprises, on its rear side, an internal thread 15 and comprises, on its inside, a cylindrical chamber into which the ampoule 5 is plugged. In a front area, the receptacle 2 is cylinder-shaped on its outside, whereby four projecting strips 47 are provided on the external surface of the receptacle 2 parallel to the cylinder axis of the receptacle 2. The ampoule 5 has a cylindrical ampoule body with a diameter that matches the inside of the receptacle 2. On the inside of the cartridge 1, the cartridge 1 forms the cylindrical internal space 11. The cylindrical geometry of the internal space 11 and of the chamber of the receptacle 2 corresponds to cylinders with a circular footprint.

A mixer 10 is fastened to the front side of the mixing rod 7 in the form of mixing vanes with a surrounding scraping ring. The presence of a scraping ring allows the areas right at the internal wall of the internal space 11 to be reached.

The receptacle 2 is bordered on its front side by a wall with multiple passages 36 as the closure of the front side, whereby the wall on the front side of the receptacle 2 closes the chamber toward the front at its circular base surface. The dispensing plunger 12 is arranged in the cylindrical internal space 11 of the cartridge 1 so as to be axially mobile. The mixing rod 7 is guided through a central passage in the dispensing plunger 12 such that the mixing rod 7 can be moved against the dispensing plunger 12 without the dispensing plunger 12 having to move in the internal space of the cartridge 1 in this context. With the receptacle 2 retracted, the mixer 10 touches against the front side of the dispensing plunger 12. As a result, the mixer 10 can reach the entire part of the internal space 11 that is bordered on the side by the cartridge 1, on the front by the cartridge lid 6, and in the rear by the dispensing plunger 12. As a result, complete mixing of the bone cement powder 4 with the monomer liquid 3 in this area is ensured.

The dispensing plunger 12 comprises multiple channels 14 passing through the dispensing plunger 12, which are arranged in a ring shape about the central passage for the mixing rod 7 in the dispensing plunger 12 and connect the front side of the dispensing plunger 12 to the rear side of the dispensing plunger 12 and thereby connect the internal space 11 of the cartridge 1 to the space 13 of the threaded tube 9. The channels 14 are covered by a ring-shaped pore filter 16. The pore filter 16 is impermeable to the bone cement powder 4 from the internal space 11 of the cartridge 1, and is permeable to the monomer liquid 3 and gases. As a result, the bone cement powder 4 is prevented from ingress into the space 13 of the threaded tube 9 and the inside of the receptacle 2.

The dispensing plunger 12 has an external diameter that is larger than the internal diameter of the internal thread 8 of the cartridge 1. The external diameter of the cylindrical dispensing plunger 12 fits the internal diameter of the internal space 11 of the cartridge 1. The dispensing plunger 12 seals the internal space 11 of the cartridge 1.

An opening facility 18 is provided on the rear side of the receptacle 2 and can be used to push the ampoule 5 in the direction of the dispensing plunger 12 in order to open the ampoule 5 on the inside of the receptacle 2 such that the monomer liquid 3 in the receptacle 2 flows out. For this purpose, the opening facility 18 comprises a sleeve 20, whereby the sleeve 20 forms a hollow cylinder in which an ampoule head of the ampoule 5 is arranged. The sleeve 20 of the opening facility 18 can thus push onto shoulders 21 of the ampoule 5 in order to push the ampoule 5 to the front in the direction of the dispensing plunger 12 and to thus open it. Because the sleeve 20 presses onto the shoulders 21, the force is guided through the ampoule body to an ampoule base 27 of the ampoule 5. The walls of the ampoule body are very stable such that the ampoule 5 will not fracture in this area. The ampoule 5 can thus be fractured at the ampoule base 27.

For this purpose, the sleeve 20 has an external thread 26 that matches the internal thread 15 of the receptacle 2. The sleeve 20 is screwed into the internal thread 15 of the receptacle 2 and can be screwed more deeply into the receptacle 2 in order to open the ampoule 5. The sleeve 20 covers the receptacle 2 in the area of the rear side of the inside of the receptacle 2.

A fixation cap 22 is screwed onto the external thread 26 of the sleeve 20. For this purpose, the sleeve 20 has a matching rear internal thread 23. The purpose of the fixation cap 22 is to affix the receptacle 2 on the threaded tube 9. For this purpose, the fixation cap 22 has a front internal thread 24 that fits on the external thread 45 of the threaded tube 9. By this design, the receptacle 2 can be affixed in the threaded tube 9 (see FIG. 6) by screwing the fixation cap 22 onto the threaded tube 9 while the receptacle 2 is fully inserted. For this purpose, the internal threads 23, 24 of the fixation cap 22, the external thread 45 of the threaded tube 9, and the external thread 26 of the sleeve 20 all have the same pitch.

For application, the bone cement applicator needs to be held or set up with the cartridge lid 6 facing downwards, as is shown in FIGS. 1 to 8.

The opening facility 18 is screwed a little, but not all the way to a limit stop, into the rear side of the receptacle 2 and is thus attached to the receptacle 2. It is important that the opening facility 18 can be screwed further into the receptacle 2 and that the sleeve 20 can be inserted more deeply into the receptacle 2 by this configuration to allow the ampoule 5 to be opened in the receptacle 2.

In order to prevent the fixation cap 22 or the opening facility 18 from rotating in the wrong direction, a reverse motion lock can be provided (not shown in FIGS. 1 to 8). The reverse motion lock prevents the fixation cap 22 from detaching and/or the opening facility 18 from detaching from the receptacle 2. The reverse motion lock can be implemented, for example, as a screw lock in the form of a locking disk or by a pair of wedge lock disks or similar structures.

In order to be able to conveniently rotate the opening facility 18 and the receptacle 2 by hand and in order to be able to conveniently insert and pull the receptacle 2 into and out of the space 13 of the threaded tube 9, the rear-side end thereof is fitted with a handle 28. For sealing the receptacle 2 with respect to the internal wall of the threaded tube 9, two circumferential seals 30 made of rubber are arranged in circumferential grooves on the front-most external circumference of the receptacle 2. The internal thread 15 of the receptacle 2 is limited and thus forms a limit stop that prevents the opening facility 18 from being screwed further into the receptacle 2.

Likewise, the external circumference of the dispensing plunger 12 has two grooves arranged on it, in which two circumferential seals 32 made of rubber are situated and which are situated at a distance from each other in the longitudinal direction. The seals 32 seal the dispensing plunger 12 with respect to the internal space 11 of the cartridge 1 and separate the internal space 11 of the cartridge 1, in which the bone cement powder 4 is arranged, from the space of the threaded tube 9.

A mandrel 34 for fracturing the ampoule 5 is arranged on the front wall of the receptacle 2 that points to the cartridge lid 6. For this purpose, the mandrel 34 points into the inside of the receptacle 2. In order to open the ampoule 5, the ampoule 5 can be pushed, by the sleeve 20, onto the mandrel 34 until the ampoule base 27 of the ampoule 5 is pushed into the ampoule body. The mandrel 34 has a blunt tip whose purpose is to have the force act on the ampoule 5 on a middle area of the ampoule base 27 such that a predetermined breakage site in the connection between the ampoule base 27 and the side walls of the ampoule body is used. The force for this purpose is exerted via the sleeve 20. The sleeve 20 has approximately the same diameter as the ampoule body of the ampoule 5. The ampoule head of the ampoule 5 is arranged on the inside of the sleeve 20 in this context. What this attains is that the ampoule 5 is not fractured in the area of the sleeve 20, because the cylindrical ampoule body is very stable, whereas the mandrel 34 can be pushed relatively easily from the front into the ampoule 5.

The mixing rod 7 is fastened to the receptacle 2 inside the mandrel 34. The mandrel 34 is connected to the receptacle 2 by a predetermined breakage site such that a pressure exerted on the mixing rod 7 causes the mixing rod 7 to sever the mandrel 34 from the receptacle 2 such that the mixing rod 7 with the mandrel 34 at the tip can be moved through the front base surface of the receptacle 2. Alternatively, an internal circular disk (not shown) of the front side of the receptacle 2 can be connected to the receptacle 2 by a thread such that the mandrel 34 can be separated, by the circular disk, from the remaining receptacle 2 by a rotation of the receptacle 2 against the mixing rod 7, which is affixed to the cartridge lid 6 for this purpose such that the mixing rod 7 again can be moved with respect to the remaining receptacle 2.

Figure 4:
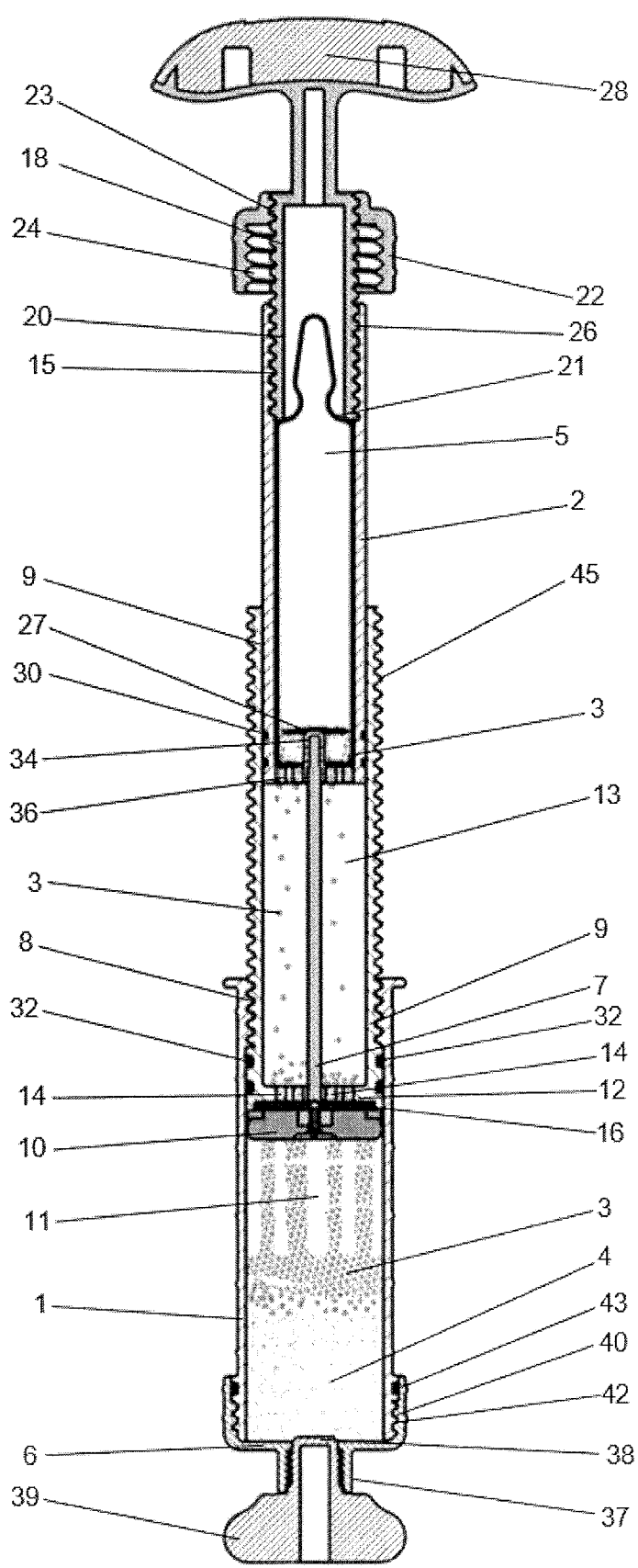
FIG. 4 shows a schematic cross-sectional view of the bone cement applicator according to FIGS. 1 to 3 having an opened monomer liquid container for illustration of the work-flow of a method according to the invention.

Multiple passages 36 are arranged about the mandrel 34 and connect the inside of the receptacle 2 to the internal space 11 of the cartridge 1. The monomer liquid 3 can flow through the passages 36 into the internal space 11 of the cartridge 1, as is shown in FIG. 4.

The front side of the cartridge 1 is closed by the cartridge lid 6. A socket 37 bordering the dispensing opening in the cartridge lid 6 is formed in the middle of the cartridge lid 6.

A closure 38 for closing the dispensing opening is screwed into the socket 37 and is thus fastened in a detachable manner. The closure 38 can be operated via wings 39 in the way of a wing screw. The cartridge lid 6 is screwed onto an external thread 42 on the front side of the cartridge 1 by an internal thread 40. The cartridge lid 6 is additionally sealed with respect to the cartridge 1 by a circumferential seal 43.

The front part of the internal space 11 of the cartridge 1 has the mixer 10 arranged in it, by which the content of the front part of the internal space 11 can be mixed through a manual motion of the mixer 10. The manual motion of the mixer 10 takes place by inserting and pulling out the receptacle 2 into and from the threaded tube 9. Namely, this action also causes the mixing rod 7, which is fastened to the front side of the receptacle 2, to be moved back and forth in a linear manner. In this context, the mixing rod 7 moves through the feedthrough in the dispensing plunger 12, and the mixer 10 fastened to the mixing rod 7 moves in the internal space 11 of the cartridge 1.

When the receptacle 2 is inserted into the threaded tube 9 up to the limit stop, the mixer 10 hits the cartridge 6 provided the threaded tube 9 is unscrewed maximally out of the rear side of the internal space 11 of the cartridge 1 up to a limit stop that is formed by the internal thread 8 of the cartridge 1 and the dispensing plunger 12. In this context, the length of the mixing rod 7 is selected appropriately such that the mixer 10 then touches against the cartridge lid 6 exactly at the front side of the internal space 11. By this configuration, the bone cement 48 at the front side of the internal space 11 can also be reached and mixed by the mixer 10.

The closure 38 projects a little ways into the internal space 11 of the cartridge 1. A recess accommodating the part of the closure 38 that projects into the internal space 11 is provided on the front side of the mixer 10 that faces the cartridge lid 6. By this configuration, the bone cement 48 touching against the closure 38 and against the cartridge lid 6 can also be mixed, and having this recess also provides a free cross-section of flow to the bone cement 48, when the closure 38 is removed and the mixer 10 touches against the cartridge lid 6 during the dispensation of the bone cement 48 (see FIG. 7).

The work-flow of a method according to the invention is illustrated in the following based on FIGS. 1 to 8. Initially, the bone cement applicator is in the starting state (see FIGS. 1 to 3 and 8). In this state, the bone cement applicator has been packaged and sterilized with ethylene oxide. The ethylene oxide can enter into the inside of the receptacle 2 through gaps in the opening facility 18 and can enter into the internal space 11 of the cartridge 1 through the passages 36, the pore filter 16, and the channels 14. The gas exchange takes place in a vacuum chamber or negative pressure chamber in this context. In this state (see FIGS. 1 to 3 and 8), the bone cement applicator is unpacked.

The bone cement applicator is held with the cartridge lid 6 downwards. Subsequently, the opening facility 18 is screwed into the receptacle 2. As before, the bone cement applicator is held with the cartridge lid 6 downwards. In this context, the sleeve 20 pushes the shoulders 21 of the ampoule 5 downwards. Subsequently, the ampoule 5 is pushed onto the mandrel 34 by its ampoule base 27, and the ampoule 5 fractures at its ampoule base 27. This state is shown in FIG. 4.

The monomer liquid 3 exits from the opened ampoule 5 in the area of the passages 36. Because the bone cement applicator is held with the cartridge lid 6 downwards, the monomer liquid 3 driven by gravity immediately flows downwards through the passages 36, the pore filter 16, and the channels 14 into the internal space 11 of the cartridge 1 and distributes in the bone cement powder 4 (see FIG. 4). In order to accelerate the monomer transfer, the receptacle 2 can be pushed into and pulled out of the threaded tube 9.

The mixing of the bone cement 48 and/or of the starting components 3, 4 of the bone cement 48 takes place by inserting and pulling the receptacle 2 into and out of the space 13 of the threaded tube 9, while the mixer 10 moves simultaneously in the internal space 11 of the cartridge 1. In this context, the mixer 10 reaches all spaces in the internal space 11 between the dispensing plunger 12 and the cartridge lid 6. The strips 47 are arranged on the outside of the receptacle 2 in order to guide this motion. The strips 47 prevent the receptacle 2 from wobbling during the mixing process.

Figure 5:
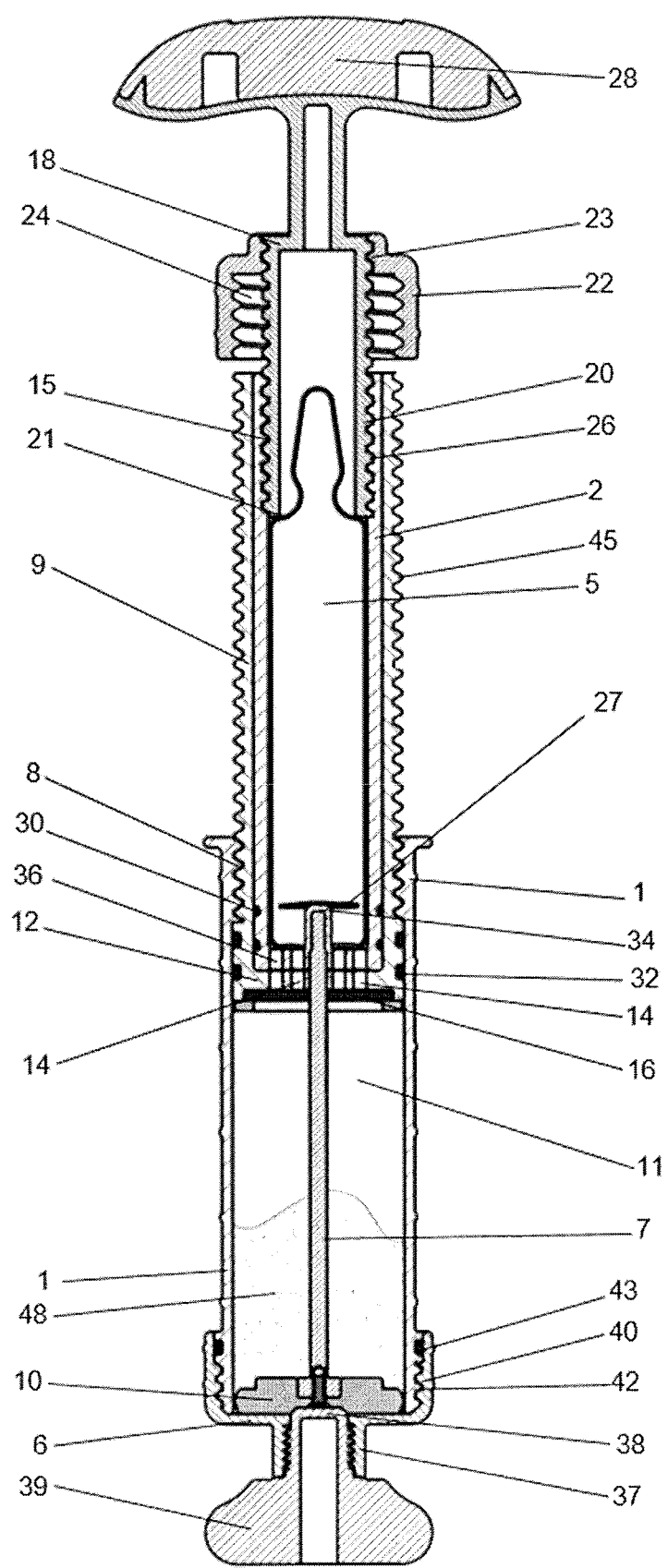
FIG. 5 shows a schematic cross-sectional view of the bone cement applicator according to FIGS. 1 to 4 having the receptacle inserted into the cartridge for illustration of the work-flow of a method according to the invention.

Finally, the bone cement 48 is mixed and the receptacle 2 is inserted fully into the threaded tube 9 such that the mixer 10 touches against the cartridge lid 6. This scenario is shown in FIG. 5.

Figure 6:
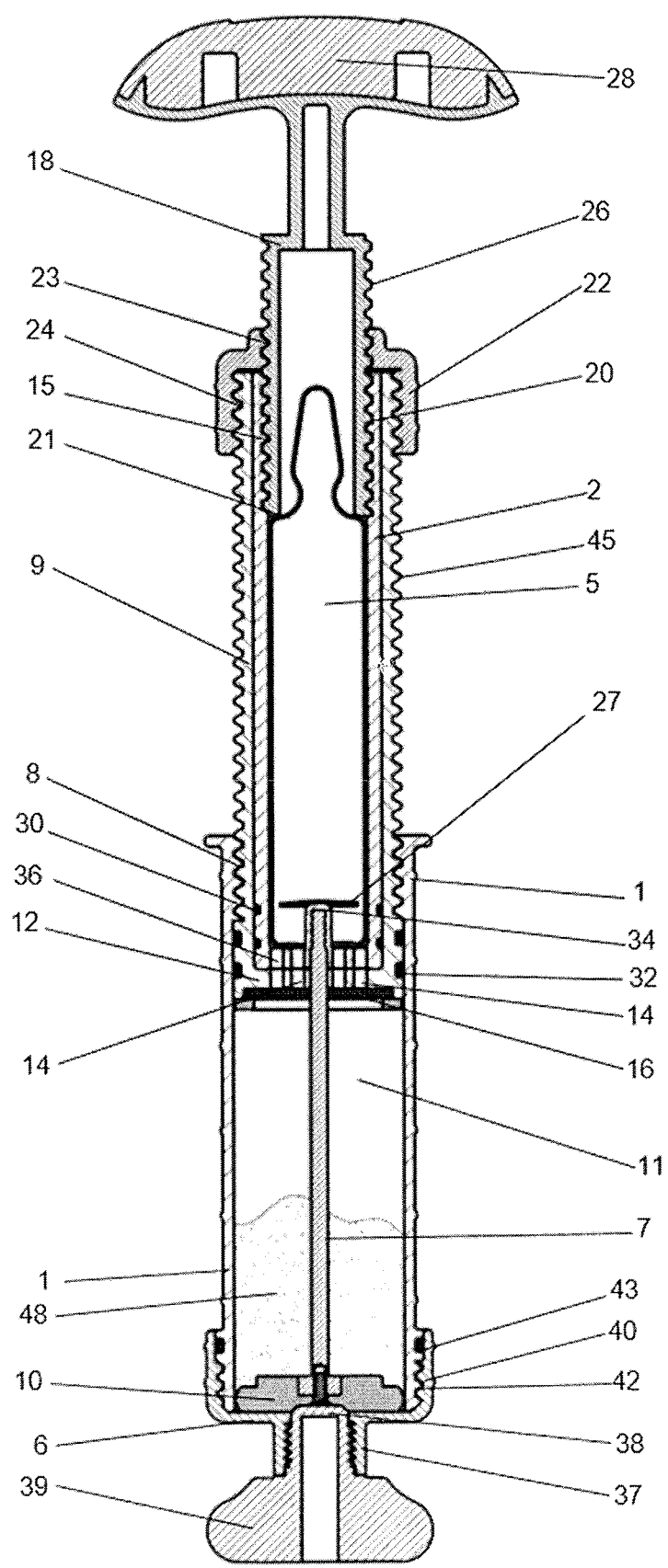
FIG. 6 shows a schematic cross-sectional view of the bone cement applicator according to FIG. 5 having the receptacle attached to a threaded tube for illustration of the work-flow of a method according to the invention.
Figure 7:
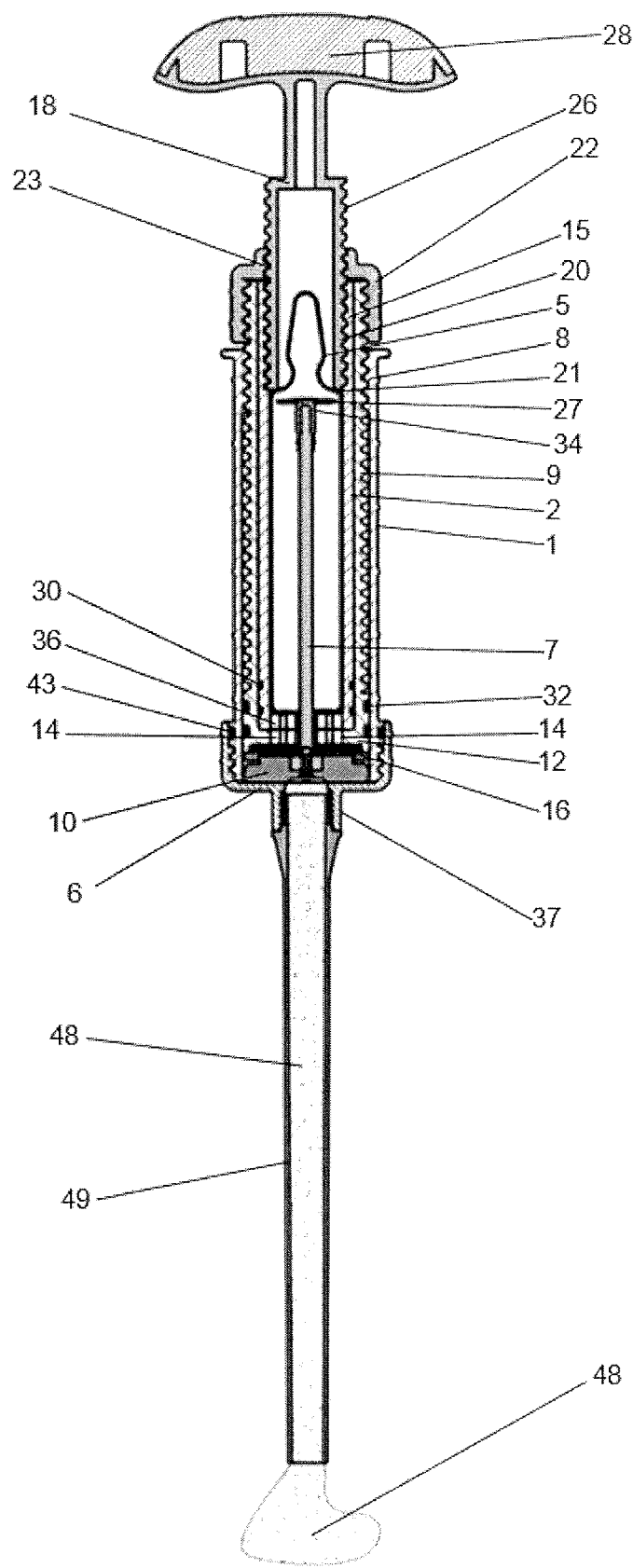
FIG. 7 shows a schematic cross-sectional view of the bone cement applicator according to FIGS. 1 to 6 having the receptacle screwed into the cartridge after dispensation of the bone cement for illustration of the work-flow of a method according to the invention.
Figure 8:
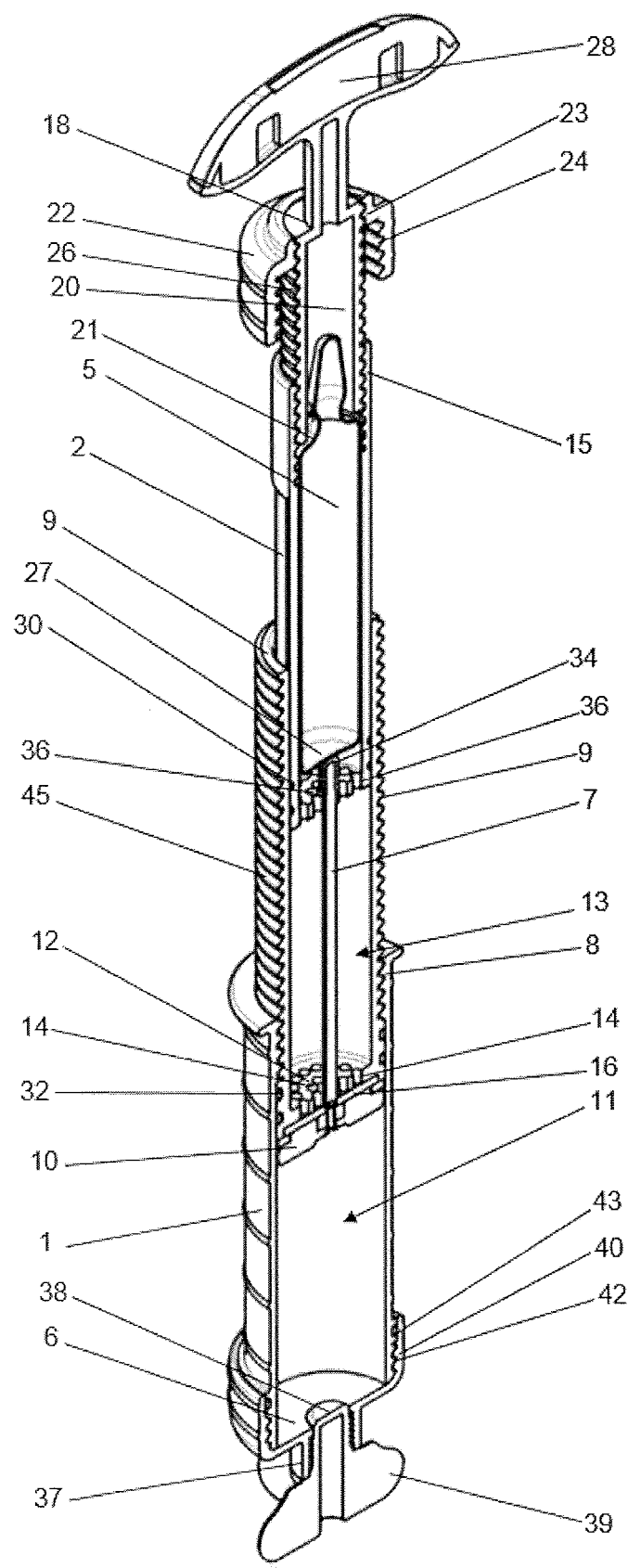
FIG. 8 shows a schematic perspective cross-sectional view of the bone cement applicator according to FIGS. 1 to 7 without the starting components in the storage condition.

For the receptacle 2 to be affixed to the threaded tube 9 such that the mixing rod 7 can be pushed into the receptacle 2, the fixation cap 22 is screwed onto the external thread 45 of the threaded tube 9. This scenario is shown in FIG. 6.

By this configuration, the receptacle 2 can be screwed into the cartridge 1 along with the threaded tube 9. As a result, the receptacle 2 can be moved forcefully against the cartridge 1. The front of the mixer 10 touches against the cartridge lid 6 such that the mixing rod 7 cannot get out of the way. The pressure transmitted by the mixing rod 7 detaches the mandrel 34 from the front wall of the receptacle 2 or the mixing rod 7 punctures the mandrel 34. Concurrently, the dispensing plunger 12 is also driven in the internal space 11 in the direction of the cartridge lid 6.

When the receptacle 2 is screwed further into the cartridge 1, the bone cement 48 is expelled out of the internal space 11 of the cartridge 1 through the opened dispensing opening. For this purpose, the closure 38 is first unscrewed from the dispensing opening and a dispensing tube 49 is screwed into the internal thread of the socket 37. For this purpose, the dispensing tube 49 has an external thread that matches the internal thread of the socket 37. The bone cement 48 is pressed between the mixer 10 and the cartridge 6, through the dispensing opening and the socket 37 into the dispensing tube 49. Subsequently, the bone cement 48 flows out of the dispensing tube 49 and is ready for application (see FIG. 7).

During the extrusion of the bone cement 48, gas inclusions in the bone cement 48 are pushed upwards into the receptacle 2 through the pore filter 16 such that a gas-depleted bone cement 48 is produced.

As an alternative to the dispensing tube 49, a hose with a trocar (not shown) can be fastened to the socket 37 through which the bone cement 48 can be applied under X-ray control in places that are difficult to access.

The features of the invention disclosed in the preceding description and in the claims, figures, and exemplary embodiments, can be essential for the implementation of the various embodiments of the invention both alone and in any combination.

Although illustrated and described above with reference to certain specific embodiments and examples, the present disclosure is nevertheless not intended to be limited to the details shown. Rather, various modifications may be made in the details within the scope and range of equivalents of the claims and without departing from the spirit of the disclosure. It is expressly intended, for example, that the steps of the methods of using the various devices disclosed above are not restricted to any particular order unless otherwise noted.

What is claimed:

1. A bone cement applicator for storage and mixing of a bone cement powder and a monomer liquid as well as for applying a pasty bone cement mixed together from the bone cement powder and the monomer liquid, the bone cement applicator comprising:
   a cartridge defining a cylindrical internal space with a cylinder axis in which the bone cement is mixed, the cartridge having a front side, a cartridge head located on the front side with a dispensing opening for expulsion of the bone cement from the internal space, a rear side situated opposite from the front side, and a thread on the rear side;
   a dispensing plunger for expelling the mixed bone cement from the internal space through the dispensing opening, the dispensing plunger having a feedthrough and a rear side that faces away from the cartridge head, whereby the bone cement powder is contained between the dispensing plunger and the cartridge head in the internal space of the cartridge;
   a threaded tube having a rear side that is opposite from the dispensing plunger and being arranged at the rear side of the dispensing plunger, the threaded tube having a counter thread that matches and engages the thread on the rear side of the cartridge and projecting out of the cartridge on the rear side of the cartridge, whereby the dispensing plunger is mobile in the internal space of the cartridge along the cylinder axis of the internal space in the direction of the cartridge head by screwing the threaded tube into or onto the cartridge;
   a receptacle defining an inside, having a front side that faces the dispensing plunger, and being both plugged into the threaded tube on the rear side of the threaded tube and mobile in the threaded tube;
   a monomer liquid container arranged on the inside of the receptacle and configured to be opened on the inside of the receptacle, the monomer liquid container containing the monomer liquid; and
   a mixing rod detachably connected to the receptacle, having a first side that faces the cartridge head and to which a mixer is fastened and a second side opposite from the first side and to which the front side of the receptacle is connected, and being arranged in the internal space of the cartridge, the mixing rod configured to be guided through the feedthrough in the dispensing plunger and to be axially mobile in the feedthrough, such that the mixing rod and the mixer can be moved in the internal space of the cartridge for mixing the bone cement powder with the monomer liquid by a motion of the receptacle against the cartridge, wherein, when the mixing rod is detached from the receptacle and the receptacle is propelled in the direction of the cartridge head the mixing rod can be pushed into the receptacle.

2. The bone cement applicator according to claim 1, wherein the thread on the rear side of the cartridge is an internal thread and the counter thread on the threaded tube is an external thread, such that the dispensing plunger is configured to move in the internal space of the cartridge axially along the cylinder axis of the internal space in the direction of the cartridge head by screwing the threaded tube into the internal space of the cartridge.

3. The bone cement applicator according to claim 1, wherein the threaded tube defines a cylindrical space that is open on the rear side of the threaded tube and the receptacle is plugged into the cylindrical space of the threaded tube from the rear side of the threaded tube.

4. The bone cement applicator according to claim 3, wherein the receptacle is sealed with respect to the cylindrical space of the threaded tube and the receptacle is configured to slide in the threaded tube.

5. The bone cement applicator according to claim 4, wherein the dispensing plunger is not movable within the internal space through a motion of the mixing rod through the feedthrough in the dispensing plunger.

6. The bone cement applicator according to claim 1, wherein the threaded tube includes, on its rear side, a cylindrical feedthrough that is sealed with respect to the receptacle and the receptacle is configured to slide in the feedthrough.

7. The bone cement applicator according to claim 6, wherein the dispensing plunger is not movable within the internal space through a motion of the mixing rod through the feedthrough in the dispensing plunger.

8. The bone cement applicator according to claim 1, wherein the mixing rod is detached from the receptacle by pressing onto the mixer touching against the cartridge head and/or by rotating or screwing the threaded tube with the receptacle against the mixer, which is secured against rotation in the internal space.

9. The bone cement applicator according to claim 1, further comprising:
  an opening facility having a sleeve with an external thread, the sleeve configured to be pushed onto the monomer liquid container on the inside of the receptacle in order to open the monomer liquid container; and
  a fixation cap having a rear internal thread with a smaller diameter than the counter thread of the threaded tube and a front internal thread that matches the counter thread of the threaded tube, affixing the receptacle to the threaded tube, and being connected via the rear internal thread to the external thread of the sleeve of the opening facility.

10. The bone cement applicator according to claim 1, further comprising an opening facility arranged on the receptacle, adapted to be operated from outside the bone cement applicator, and configured to open the monomer liquid container on the inside of the receptacle.

11. The bone cement applicator according to claim 1, wherein the inside of the receptacle is connected in a liquid-permeable manner to the internal space of the cartridge, the front side of the receptacle has at least one liquid-permeable passage, and the dispensing plunger has at least one liquid-permeable channel.

12. The bone cement applicator according to claim 1, wherein the cartridge head is a cartridge lid having a socket and the cartridge lid is configured to be screwed onto the cartridge, the cartridge lid seals the internal space of the cartridge at the front side of the cartridge in a gas-tight and liquid-tight manner, and the dispensing opening is arranged in the socket of the cartridge lid.

13. The bone cement applicator according to claim 1, further comprising a mandrel for opening the monomer liquid container, the mandrel arranged on a side of the receptacle that points into the inside of the receptacle.

14. The bone cement applicator according to claim 1, wherein the mixing rod has a circular disk with an external thread and the receptacle has a front side that faces the cartridge head and an internal thread that matches the external thread on the circular disk, whereby the external thread of the circular disk engages the matching internal thread of the front side of the receptacle to connect the mixing rod to the receptacle.

15. The bone cement applicator according to claim 14, wherein the external thread of the circular disk and the internal thread of the front side of the receptacle are left-hand threads.

* * * * *